(12) United States Patent
Nishiyama et al.

(10) Patent No.: US 6,340,767 B1
(45) Date of Patent: Jan. 22, 2002

(54) PROCESSES FOR THE PREPARATION OF 5-HYDROXY-3-OXOPENTANOIC ACID DERIVATIVES

(75) Inventors: Akira Nishiyama; Kenji Inoue, both of Kakogawa (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/762,215
(22) PCT Filed: Jun. 2, 2000
(86) PCT No.: PCT/JP00/03574
  § 371 Date: Apr. 5, 2001
  § 102(e) Date: Apr. 5, 2001
(87) PCT Pub. No.: WO00/75099
  PCT Pub. Date: Dec. 14, 2000

(30) Foreign Application Priority Data

Jun. 4, 1999 (JP) ............................................. 11-158033
Feb. 1, 2000 (JP) ........................................ 2000-023084

(51) Int. Cl.$^7$ .............................................. C07C 51/00
(52) U.S. Cl. .......................... 554/115; 560/174; 554/115
(58) Field of Search ................................. 554/154, 115; 560/174

(56) References Cited

PUBLICATIONS

Nskata et al., "Synthetic study of marin macrolide swinholide", Chem. Pham. Bull., vol. 42, No. 11, p. 2403–05, 1994.*

* cited by examiner

*Primary Examiner*—Deborah D. Carr
(74) *Attorney, Agent, or Firm*—Connolly Bove Lodge & Hutz LLP

(57) ABSTRACT

This invention provides a process for producing a 5-hydroxy-3-oxopentanoic acid, a useful pharmaceutical intermediate, easily from a readily available, inexpensive starting material without using any extraordinary production equipment such as a very-low-temperature reactor.

Thus, this invention provides a process for producing a 5-hydroxy-3-oxopentanoic acid
  which comprises permitting a lithium amide to act upon a mixture of an acetic acid ester and a 3-hydroxypropionic acid derivative at not below −20° C.

Further, this invention also provides a process for producing a 5-hydroxy-3-oxopentanoic acid
  which comprises treating a mixture of an acetic acid ester and a 3-hydroxypropionic acid derivative with a Grignard reagent to prepare a mixture of a compound and an acetic acid ester of the above formula (I),
  and permitting a lithium amide to act upon the mixture at a temperature not below −20° C.

20 Claims, No Drawings

PROCESSES FOR THE PREPARATION OF 5-HYDROXY-3-OXOPENTANOIC ACID DERIVATIVES

This application is a 371 of PCT/JP00/03574 filed Jun. 2, 2000.

TECHNICAL FIELD

The present invention relates to a process for producing a 5-hydroxy-3-oxopentanoic acid derivative which is of value as a pharmaceutical intermediate, particularly an intermediate of an HMG-COA reductase inhibitor.

BACKGROUND ART

The hitherto-known process for producing a 5-hydroxy-3-oxopentanoic acid derivative includes the following processes.

(1) The process in which 3-hydroxypropionic acid imidazolide prepared from 3-hydroxypropionic acid and diimidazoyl ketone is coupled to a malonic acid monoester monomagnesium salt (Synthesis, 1992, 4, 403–408).

(2) The process in which a lithium enolate prepared from tert-butyl acetate and lithium diisopropylamide is reacted with a 3-hydroxypropionic acid ester (Japanese Kokai Publication Hei-8-198832, Chem. Pharm. Bull., 1994, 42 (11), 2403–2405, Tetrahedron Lett., 1993, 49 (10), 1997–2010, Tetrahedron, 1990, 46 (29), 7283–7288, Tetrahedron Asymmetry, 1990, 1 (5), 307–310, Tetrahedron Lett., 1989, 30 (38), 5115–5118, Tetrahedron Lett., 1987, 28 (13), 1385–1388, Synthesis, 1985, (1), 45–48).

However, the prior art (1) requires an expensive starting material while the prior art (2) involves a very low reaction temperature of −78° C. to −40° C., so that neither is a favorable process for commercial-scale production.

DISCLOSURE OF INVENTION

The object of the present invention, in the above perspective, is to provide a production process by which a 5-hydroxy-3-oxopentanoic acid derivative of the following formula (IV), a useful pharmaceutical intermediate, can be prepared easily from a readily available, inexpensive starting material without using any extraordinary production equipment such as a very-low-temperature reactor:

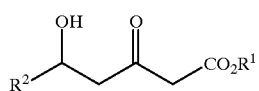

(IV)

wherein $R^1$ represents any of an alkyl group of 1 to 12 carbon atoms, an aryl group of 6 to 12 carbon atoms and an aralkyl group of 7 to 12 carbon atoms; and $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group.

The inventors of the present invention made intensive investigations in view of the above state of the art and found that, starting with a readily available, inexpensive starting material, a 5-hydroxy-3-oxopentanoic acid derivative of the following formula (IV) can be produced without using any special equipment such as a very-low-temperature reactor:

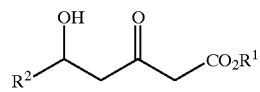

(IV)

wherein $R^1$ represents any of an alkyl group of 1 to 12 carbon atoms, an aryl group of 6 to 12 carbon atoms and an aralkyl group of 7 to 12 carbon atoms; and $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group.

The present invention, therefore, relates to a process for producing a 5-hydroxy-3-oxopentanoic acid derivative of the following formula (IV):

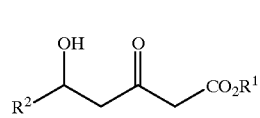

(IV)

wherein $R^1$ represents any of an alkyl group of 1 to 12 carbon atoms, an aryl group of 6 to 12 carbon atoms and an aralkyl group of 7 to 12 carbon atoms; and $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group, which comprises permitting a lithium amide of the following formula (III):

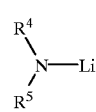

(III)

wherein $R^4$ and $R^5$ may be the same or different and each represents any of an alkyl group of 1 to 12 carbon atoms, an aryl group of 6 to 12 carbon atoms, an aralkyl group of 7 to 12 carbon atoms, and a silyl group to act upon a mixture of an acetic acid ester of the following formula (I) and a 3-hydroxypropionic acid derivative of the following formula (II) at a temperature not below −20° C.:

(I)

wherein $R^1$ represents any of an alkyl group of 1 to 12 carbon atoms, an aryl group of 6 to 12 carbon atoms and an aralkyl group of 7 to 12 carbon atoms:

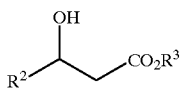

(II)

wherein $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group; $R^3$ represents any of an alkyl group of 1 to 12 carbon atoms, an aryl group of 6 to 12 carbon atoms and an aralkyl group of 7 to 12 carbon atoms; and $R^2$ and $R^3$ may be joined to each other to form a ring.

The invention further relates to a process for producing a 5-hydroxy-3-oxopentanoic acid derivative of the following formula (IV):

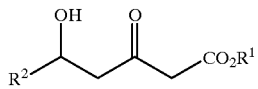

(IV)

wherein $R^1$ represents any of an alkyl group of 1 to 12 carbon atoms, an aryl group of 6 to 12 carbon atoms and an aralkyl group of 7 to 12 carbon atoms; and $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group, which comprises treating a mixture of an acetic acid ester of the following formula (I) and a 3-hydroxypropionic acid derivative of the following formula (II):

(I)

wherein $R^1$ represents any of an alkyl group of 1 to 12 carbon atoms, an aryl group of 6 to 12 carbon atoms and an aralkyl group of 7 to 12 carbon atoms:

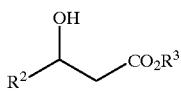

(II)

wherein $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group; $R^3$ represents any of an alkyl group of 1 to 12 carbon atoms, an aryl group of 6 to 12 carbon atoms and an aralkyl group of 7 to 12 carbon atoms; and $R^2$ and $R^3$ may be joined to each other to form a ring with a Grignard reagent of the following formula (V):

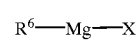

(V)

wherein $R^6$ represents any of an alkyl group of 1 to 12 carbon atoms, an aryl group of 6 to 12 carbon atoms and an aralkyl group of 7 to 12 carbon atoms; and X represents a halogen atom to prepare a mixture of a compound of the following formula (VI) and an acetic acid ester of the above formula (I):

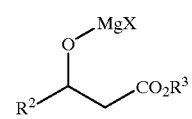

(VI)

wherein $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group; $R^3$ represents any of an alkyl group of 1 to 12 carbon atoms, an aryl group of 6 to 12 carbon atoms and an aralkyl group of 7 to 12 carbon atoms; $R^2$ and $R^3$ may be joined to each other to form a ring; and X represents a halogen atom, and permitting a lithium amide of the following formula (III):

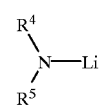

(III)

wherein $R^4$ and $R^5$ maybe the same or different and each represents any of an alkyl group of 1 to 12 carbon atoms, an aryl group of 6 to 12 carbon atoms, an aralkyl group of 7 to 12 carbon atoms, and a silyl group, to act upon the mixture at a temperature not below −20° C.

The present invention further relates to a process for producing a 5-hydroxy-3-oxopentanoic acid derivative of the following formula (IV):

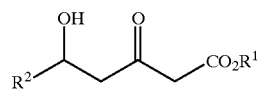

(IV)

wherein $R^1$ represents any of an alkyl group of 1 to 12 carbon atoms, an aryl group of 6 to 12 carbon atoms and an aralkyl group of 7 to 12 carbon atoms; and $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group, which comprises permitting a lithium amide of the following formula (III):

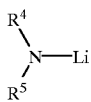

wherein $R^4$ and $R^5$ maybe the same or different and each represents any of an alkyl group of 1 to 12 carbon atoms, an aryl group of 6 to 12 carbon atoms, an aralkyl group of 7 to 12 carbon atoms and a silyl group, to act upon a mixture of an acetic acid ester of the following formula (I) and a compound of the following formula (VI) at a temperature not below −20° C.:

wherein $R^1$ represents any of an alkyl group of 1 to 12 carbon atoms, an aryl group of 6 to 12 carbon atoms and an aralkyl group of 7 to 12 carbon atoms:

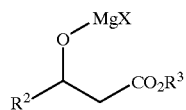

wherein $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group; $R^3$ represents any of an alkyl group of 1 to 12 carbon atoms, an aryl group of 6 to 12 carbon atoms and an aralkyl group of 7 to 12 carbon atoms; $R^2$ and $R^3$ may be joined to each other to form a ring; and X represents a halogen atom.

The present invention is now described in detail.

The acetic acid ester is represented by the general formula (I):

Here, $R^1$ represents any of an alkyl group of 1 to 12 carbon atoms, an aryl group of 6 to 12 carbon atoms and an aralkyl group of 7 to 12 carbon atoms. As specific examples, there can be mentioned methyl, ethyl, isopropyl, tert-butyl, n-octyl, phenyl, naphthyl, p-methoxyphenyl, benzyl, and p-nitrobenzyl, among others. Preferred is t-butyl.

The 3-hydroxypropionic acid derivative is represented by the general formula (II):

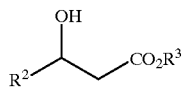

Here, $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group. As specific examples, there can be mentioned methyl, ethyl, isopropyl, tert-butyl, chloromethyl, bromomethyl, cyanomethyl, benzyloxymethyl, trityloxymethyl, tert-butyldiphenylsilyloxymethyl, dimethoxymethyl, 1,3-dithian-2-yl, 1,3-dithiolan-2-yl, vinyl, 2-phenylvinyl, 2-phenylethyl, 2-carbobenzyloxyaminoethyl, phenyl, naphthyl, p-methoxyphenyl, benzyl, p-nitrobenzyl, cyano, carboxy and tert-butoxycarbonyl, among others. Preferred are methyl, ethyl, isopropyl, tert-butyl, chloromethyl, cyanomethyl, benzyloxymethyl, trityloxymethyl, tert-butyldiphenylsilyloxymethyl, dimethoxymethyl, vinyl, 2-phenylethyl, phenyl, naphthyl, p-methoxyphenyl, benzyl and p-nitrobenzyl, among others. More preferred are chloromethyl, cyanomethyl and benzyloxymethyl.

As the substituents on the alkyl, alkenyl, aryl and aralkyl groups each represented by the above $R^2$, there can be mentioned halogen, cyano, $C_{7-19}$ aralkyloxy, $C_{1-12}$ alkoxy, $C_{6-12}$ aryl, nitro, siloxy, N-protected amino, $C_{1-12}$ alkylthio, $C_{6-12}$ arylthio and $C_{7-12}$ aralkylthio, among others. The number of substituents may be 0 to 3. The number of carbon atoms of said alkoxycarbonyl group in the above $R^2$ may for example be 2 to 13.

$R^3$ represents any of an alkyl group of 1 to 12 carbon atoms, an aryl group of 6 to 12 carbon atoms and an aralkyl group of 7 to 12 carbon atoms. Specifically, methyl, ethyl, isopropyl, tert-butyl, n-octyl, phenyl, naphthyl, p-methoxyphenyl, benzyl, p-nitrobenzyl, etc. can be mentioned. Preferred is methyl or ethyl.

$R^2$ and $R^3$ may be joined to each other to form a ring; $R^2$ and $R^3$ specifically may jointly represent a methylene group, an ethylene group, a propylene group or the like, preferably a methylene group.

The lithium amide is represented by the general formula (III):

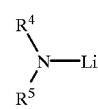

Here, $R^4$ and $R^5$ may be the same or different and each represents any of an alkyl group of 1 to 12 carbon atoms, an aryl group of 6 to 12 carbon atoms, an aralkyl group of 7 to 12 carbon atoms, and a silyl group. Specifically, there can be mentioned methyl, ethyl, isopropyl, tert-butyl, cyclohexyl, n-octyl, phenyl, naphthyl, p-methoxyphenyl, benzyl, p-nitrobenzyl, trimethylsilyl, triethylsilyl and phenyldimethylsilyl, among others. Preferred is isopropyl.

The Grignard reagent is represented by the general formula (V):

Here, $R^6$ represents any of an alkyl group of 1 to 12 carbon atoms, an aryl group of 6 to 12 carbon atoms and an aralkyl group of 7 to 12 carbon atoms. Specifically, there can be mentioned methyl, ethyl, n-propyl, isopropyl, n-butyl, tert-butyl, n-octyl, phenyl, naphthyl, p-methoxyphenyl, benzyl and p-nitrobenzyl, among others. Preferred are methyl, ethyl, isopropyl, n-butyl, tert-butyl, etc. More preferred is tert-butyl. X represents a halogen atom. Preferred are chloro, bromo and iodo. More preferred is chloro.

The process for producing a 5-hydroxy-3-oxopentanoic acid derivative in accordance with the present invention is now described.

When a reaction involving an enolate such as an acetate-derived enolate is conducted at a non-very-low reaction temperature, for example not below −20° C., the self-condensation of the enolate proceeds predominantly to remarkably sacrifice the rate of conversion of the objective reaction. However, in the process developed by the present inventors, the self-condensation of the acetic enolate can be minimized so that the objective reaction can be carried out in high yield.

Thus, this reaction is carried out by adding a solution of a lithium amide dropwise to a mixed solution of an acetic acid ester and a 3-hydroxypropionic acid derivative. The acetic acid ester is not particularly restricted but includes, for example, methyl acetate, ethyl acetate, isopropyl acetate, t-butyl acetate, phenyl acetate and benzyl acetate. Preferred is t-butyl acetate. The amount of use of this acetic acid ester is preferably 1 to 5 molar equivalents, and more preferably 1.5 to 3 molar equivalents, based on the 3-hydroxypropionic acid derivative. The 3-hydroxypropionic acid derivative is not particularly restricted but includes methyl 3-hydroxypropionate, ethyl 3-hydroxybutanoate, ethyl 3-hydroxypentanoate, ethyl 4-chloro-3-hydroxybutanoate, ethyl 4-bromo-3-hydroxybutanoate, 4-cyano-3-hydroxybutanoate, ethyl 4-benzyloxy-3-hydroxybutanoate, ethyl 4-trityloxy-3-hydroxybutanoate, ethyl 4-tert-butyldiphenyloxy-3-hydroxybutanoate, ethyl 3-cyano-3-hydroxypropionate, methyl 4,4-dimethoxy-3-hydroxybutanoate, ethyl 5-phenyl-3-hydroxyhexanoate, ethyl 5-carbobenzyloxyamino-3-hydroxyhexanoate, phenyl 3-phenyl-3-hydroxypropionate, methyl 3-naphthyl-3-hydroxypropionate, benzyl 4-phenyl-3-hydroxybutanoate, ethyl 4-p-nitrophenyl-3-hydroxybutanoate and 3-hydroxybutyrolactone, among others.

Furthermore, in accordance with the present invention, an optically active 3-hydroxypropionic acid derivative can be used as the starting material to give the corresponding objective compound without being sacrificed in optical purity. Therefore, more preferred are optically active ethyl 3-hydroxybutanoate, ethyl 4-chloro-3-hydroxybutanoate, ethyl 4-cyano-3-hydroxybutanoate, ethyl 4-benzyloxy-3-hydroxybutanoate, and 3-hydroxybutyrolactone, among others.

These optically active 3-hydroxypropionic acid derivatives can be easily prepared in accordance with the known production processes. For example, (3S)-4-chloro-3-hydroxybutyric acid ethyl ester can be produced by the process described in WO 98/35025; (3S)-4-cyano-3-hydroxybutyric acid ethyl ester can be produced by the process disclosed in Japanese Kohyo Publication Hei-7-500105; and (S)-3-hydroxybutyrolactone can be produced by the process described in Synthetic Communication 16, 183, 1986.

The lithium amide is not particularly restricted but includes lithium dimethylamide, lithium diethylamide, lithium diisopropylamide, lithium di-tert-butylamide, lithium dicyclohexylamide, lithium 2,2,6,6-tetramethylpiperidine, lithium diphenylamide, lithium dibenzylamide and lithium hexamethyldisilazide, among others. Preferred is lithium diisopropylamide. These can be used each alone or two or more of them can be used in combination. The amount of use of the lithium amide relative to the 3-hydroxypropionic acid derivative is preferably 1 to 10 molar equivalents, more preferably 2 to 5 molar equivalents.

The yield of the objective compound can be increased by conducting this reaction in the presence of a magnesium halide. Thus, the reaction can be conducted with greater advantage by adding a solution of a lithium amide to a mixed solution containing the acetic acid ester, 3-hydroxypropionic acid derivative and magnesium halide. The magnesium halide is not particularly restricted but includes, for example, magnesium chloride, magnesium bromide and magnesium iodide. Preferred is magnesium chloride. The amount of use of the magnesium halide relative to the 3-hydroxypropionic acid derivative is preferably 0.5 to 10 molar equivalents, more preferably 1 to 5 molar equivalents.

Referring, further, to this reaction, the yield of the objective compound can be further improved by treating the 3-hydroxypropionic acid derivative with a Grignard reagent in advance to prepare the halomagnesium alkoxide compound and, then, conducting the reaction. In this case, the Grignard reagent is added dropwise to the 3-hydroxypropionic acid derivative to prepare the halomagnesium alkoxide compound and, after mixing the acetic acid ester, the lithium amide solution is added dropwise to carry out the reaction. As an alternative, the treatment with the Grignard reagent may be carried out in the presence of the acetic acid ester. Thus, the reaction can be conducted by adding the Grignard reagent to a mixed solution containing the acetic acid ester and 3-hydroxypropionic acid derivative and, then, adding the lithium amide solution dropwise to the reaction mixture. This Grignard reagent is not particularly restricted but includes for example methylmagnesium bromide, ethylmagnesium iodide, isopropylmagnesium chloride, n-butylmagnesium chloride and tert-butylmagnesium chloride. Preferred is tert-butylmagnesium chloride. The amount of use of the Grignard reagent relative to the 3-hydroxypropionic acid derivative is preferably 0.5 to 5 molar equivalents. More preferred is 1 to 2 molar equivalents.

The solvent which can be used for this reaction may for example be an aprotic organic solvent. The organic solvent mentioned above includes hydrocarbon solvents such as benzene, toluene, n-hexane, cyclohexane, etc.; ether solvents such as diethyl ether, tetrahydrofuran, 1,4-dioxane, methyl t-butyl ether, dimethoxymethane, ethylene glycol dimethyl ether, etc.; halogen-containing solvents such as methylene chloride, chloroform, carbon tetrachloride, 1,2-dichloroethane, etc.; and aprotic polar solvents such as dimethylpropyleneurea, N-methylpyrrolidone, hexamethylphosphoric triamide, etc., among others. These solvents may be used each alone or two or more of them may be used in a suitable combination. Preferred, among the above-mentioned solvents, are hydrocarbon solvents, such as benzene, toluene, n-hexane, cyclohexane, etc., and ether solvents, such as diethyl ether, tetrahydrofuran, 1,4-dioxane, methyl t-butyl ether, dimethoxymethane, ethylene glycol dimethyl ether and so on.

The reaction temperature for this reaction is preferably −20° C. to 80° C. More preferred is −10° C. to 40° C.

The aftertreatment of this reaction may be the routine aftertreatment for recovery of the reaction product from a reaction mixture. A typical procedure may comprise blending the reaction mixture at completion of the reaction with an aqueous solution of the common inorganic or organic acid, such as hydrochloric acid, sulfuric acid, nitric acid, acetic acid and citric acid, and carrying out an extraction with the common extractant such as ethyl acetate, diethyl ether, methylene chloride, toluene and hexane. From the extract obtained, the reaction solvent and extractant are distilled by heating under reduced pressure, for instance, whereby the objective product can be isolated. The objective product thus obtained can be purified by the routine technique, such as crystallization, fractional distillation, column chromatography and/or the like to further enhance its purity.

BEST MODE FOR CARRYING OUT THE INVENTION

The following examples illustrate the present invention in further detail without defining its metes and bounds.

Example 1

Tert-butyl 6-benzyloxy-5-hydroxy-3-oxohexanoate

Under argon gas, a solution composed of 5.01 g (49.5 mmol) of diisopropylamine and 5 mL of tetrahydrofuran was added dropwise to 30 mL (45 mmol) of n-butyllithium/hexane (1.5 mol/L) with stirring at 5° C. and the mixture was stirred for 1 hour to prepare a lithium diisopropylamide solution.

In 8.0 ml of tetrahydrofuran were dissolved 2.38 g (10 mmol) of ethyl 4-benzyloxy-3-hydroxybutyrate and 2.32 g (20 mmol) of tert-butyl acetate, and the solution was stirred in an argon atmosphere at 0 to 5° C. To this solution, the lithium diisopropylamide solution prepared above was added dropwise over 30 minutes, and the mixture was further stirred at 5 to 20° C. for 16 hours.

In a separate vessel, 35 mL of 3 N-hydrochloric acid was mixed with 30 mL of ethyl acetate under stirring and the above reaction mixture was poured. After standing, the organic layer was separated, washed with saturated aqueous sodium chloride solution, and dried over anhydrous magnesium sulfate. The solvent was then distilled off under reduced pressure.

The residue was purified by silica gel column chromatography (Merck's Kieselgel 60, hexane:ethyl acetate=4:1) to give 1698 mg of tert-butyl 6-brenzyloxy-5-hydroxy-3-oxohexanoate (yellow oil) in 55% yield.

$^1$H-NMR (CDCl$_3$, 400 MHz/ppm): 1.46 (9H, s) , 2.75 (2H, d) , 2.93 (1H, bs), 3.39 (2H, s) , 3.47 (2H, m) , 4.28 (1H, m) , 4.55 (2H, s), 7.29–7.36 (5H, m)

$^{13}$C-NMR (CDCl$_3$, 400 MHz/ppm): 27.9, 46.1, 51.1, 66.6, 73.1, 73.3, 82.1, 127.7, 127.8, 128.4, 137.8, 166.1, 203.0

Example 2

Tert-butyl 6-benzyloxy-5-hydroxy-3-oxohexanoate

Under argon gas, a solution composed of 3.90 g (38.5 mmol) of diisopropylamine and 3 mL of tetrahydrofuran was added dropwise to 22.9 mL (35 mmol) of n-butyllithium/hexane (1.5 mol/L) with stirring at 5° C. and the mixture was stirred for 1 hour to prepare a lithium diisopropylamide solution.

In 3.0 ml of tetrahydrofuran were dissolved 2.38 g (10 mmol) of ethyl 4-benzyloxy-3-hydroxybutyrate and 2.32 g (20 mmol) of tert-butyl acetate, and the solution was stirred in an argon atmosphere at 0 to 5° C. To this solution was added 5.7 g (10 mmol) of a solution of tert-butylmagnesium chloride in toluene/tetrahydrofuran (1:2.5 by weight) (1.75 mol/kg) dropwise over 10 minutes, and the mixture was further stirred at 5° C. for 50 minutes. To this, the lithium diisopropylamide solution prepared above was added dropwise over 30 minutes, and the mixture was further stirred at 5 to 20° C. for 16 hours.

In a separate vessel, 30 mL of 3 N-hydrochloric acid was mixed with 30 mL of ethyl acetate under stirring and the above reaction mixture was poured. After standing, the organic layer was separated, washed with saturated aqueous sodium chloride solution, and dried over anhydrous magnesium sulfate. The solvent was then distilled off under reduced pressure.

The residue was purified by silica gel column chromatography (Merck's Kieselgel 60, hexane:ethyl acetate=4:1) to give 2420 mg of tert-butyl 6-brenzyloxy-5-hydroxy-3-oxohexanoate (red oil) in 79% yield.

Example 3

Tert-butyl (5S)-6-chloro-5-hydroxy-3-oxohexanoate

Under argon gas, a solution composed of 2.67 g (26.4 mmol) of diisopropylamine and 5 mL of tetrahydrofuran was added dropwise to 15 mL (24 mmol) of n-butyllithium/hexane (1.6 mol/L) with stirring at 5° C. and the mixture was stirred for 1 hour to prepare a lithium diisopropylamide solution.

In 5.0 ml of tetrahydrofuran were dissolved 1.0 g (6.0 mmol) of ethyl (3S)-4-chloro-3-hydroxybutyrate and 2.78 g (24 mmol) of tert-butyl acetate, and the solution was stirred in an argon atmosphere at 0 to 5° C. To this the lithium diisopropylamide solution prepared above was added dropwise over 20 minutes, and the mixture was further stirred at 5 to 20° C. for 16 hours.

In a separate vessel, 6.31 g of concentrated hydrochloric acid, 20 g of water, and 20 mL of ethyl acetate were mixed together under stirring and the above reaction mixture was poured. After standing, the organic layer was separated, washed with saturated aqueous sodium chloride solution, and dried over anhydrous magnesium sulfate. The solvent was then distilled off under reduced pressure.

The residue was purified by silica gel column chromatography (Merck's Kieselgel 60, hexane:ethyl acetate=4:1) to give 86 mg of tert-butyl (5S)-6-chloro-5-hydroxy-3-oxohexanoate (colorless oil) in 6% yield.

$^1$H-NMR (CDCl$_3$, 400 MHz/ppm): 1.48 (9H, s), 2.84 (1H, dd), 2.91 (1H, dd), 3.05 (1H, bs), 3.41 (2H, s), 3.55–3.64 (2H, m), 4.28–4.36 (1H, m)

Example 4

Tert-butyl (5S)-6-chloro-5-hydroxy-3-oxohexanoate

Under argon gas, a solution composed of 10.0 g (99 mmol) of diisopropylamine and 20 mL of tetrahydrofuran was added dropwise to 56.3 mL (90 mmol) of n-butyllithium/hexane (1.6 mol/L) with stirring at 5° C. and the mixture was stirred for 1 hour to prepare a lithium diisopropylamide solution.

In 10.0 ml of tetrahydrofuran were suspended 3.0 g (18.0 mmol) of ethyl (3S)-4-chloro-3-hydroxybutyrate, 5.22 g (45 mmol) of tert-butyl acetate and 6.86 g (72 mmol) of magnesium chloride, and the suspension was stirred in an argon atmosphere at 0 to 5° C. To this solution, the lithium diisopropylamide solution prepared above was added dropwise over 1 hour, and the mixture was further stirred at 25° C. for 3 hours.

In a separate vessel, 21.7 g of concentrated hydrochloric acid, 30 g of water, and 30 mL of ethyl acetate were mixed together under stirring and the above reaction mixture was poured. After standing, the organic layer was washed with water twice and the solvent was distilled off under reduced pressure to give 5.62 g of a red oil containing tert-butyl (5S)-6-chloro-5-hydroxy-3-oxohexanoate.

This oil was analyzed by high-performance liquid chromatography (column: Nacalai Tesque, Cosmosil 5CN-R (4.6 mm×250 mm), eluent: water/acetonitrile=9/1, flow rate: 1.0 ml/min, detection: 210 nm, column temperature: 40° C. The reaction yield was 65%.

Example 5

Tert-butyl (5S)-6-chloro-5-hydroxy-3-oxohexanoate

Under argon gas, a solution composed of 26.71 g (264 mmol) of diisopropylamine and 18.8 g of tetrahydrofuran was added dropwise to 150 mL (240 mmol) of n-butyllithium/hexane (1.6 mol/L) with stirring at 5 ( and the mixture was stirred to prepare a lithium diisopropylamide solution.

In 20 mL of tetrahydrofuran were dissolved 12.5 g (75 mmol) of ethyl (3S)-4-chloro-3-hydroxybutyrate and 17.4 g (150 mmol) of tert-butyl acetate, and the solution was stirred in an argon atmosphere at 0 to 5° C. To this solution was added 42.9 g (75 mmol) of a solution of tert-butylmagnesium chloride in toluene/tetrahydrofuran (1:2.5, by weight) (1.8 mol/kg) dropwise over 30 minutes, and the mixture was further stirred at 5° C. for 30 minutes. Then, the lithium diisopropylamide solution prepared above was added dropwise over 3 hours and the mixture was further stirred at 5° C. for 16 hours.

In a separate vessel, 60.38 g of concentrated hydrochloric acid, 31.3 g of water, and 50 mL of ethyl acetate were mixed together under stirring and the above reaction mixture was poured. After standing, the organic layer was separated, washed with water twice and the solvent was distilled off under reduced pressure to give 22.0 g of a red oil containing tert-butyl (5S)-6-chloro-5-hydroxy-3-oxohexanoate.

The reaction yields as analyzed by the method described in Example 3 was 78%.

Example 6

Tert-butyl (5S)-6-cyano-5-hydroxy-3-oxohexanoate

Under argon gas, a solution composed of 5.01 g (49.5 mmol) of diisopropylamine and 5 mL of tetrahydrofuran was added dropwise to 30 mL (45 mmol) of n-butyllithium/hexane (1.5 mol/L) with stirring at 5° C. and the mixture was stirred for 1 hour to prepare a lithium diisopropylamide solution.

In 8.0 ml of tetrahydrofuran were suspended 1.57 g (10 mmol) of ethyl (3S)-4-cyano-3-hydroxybutyrate and 2.32 g (20 mmol) of tert-butyl acetate, and the suspension was stirred in an argon atmosphere at 0 to 5° C. To this solution, the lithium diisopropylamide solution prepared above was added dropwise over 30 minuets, and the mixture was further stirred at 5 to 2° C. for 16 hours.

In a separate vessel, 35 mL of 3 N-hydrochloric acid was mixed with 30 mL of ethyl acetate under stirring and the above reaction mixture was poured. After standing, the organic layer was separated, washed with saturated aqueous sodium chloride solution, and dried over anhydrous magnesium sulfate. The solvent was then distilled off under reduced pressure.

The residue was purified by silica gel column chromatography (Merck's Kieselgel 60, hexane:ethyl acetate=3:1) to give 586 mg of tert-butyl (5S)-6-cyano-5-hydroxy-3oxohexanoate (red oil) in 26% yield.

$^1$H-NMR (CDCl$_3$, 400 MHz/ppm): 1.48 (9H, 2), 2.61 (2H, m), 2.90 (2H, m), 3.42 (3H, s), 4.41 (1H, m)

$^{13}$C-NMR (CDCl$_3$, 400 MHz/ppm): 25.0, 28.0, 48.0, 50.9, 63.6, 82.8, 117.0, 166.0, 202.8

Example 7

Tert-butyl (5S)-6-cyano-5-hydroxy-3-oxohexanoate

Under argon gas, a solution composed of 5.01 g (49.5 mmol) of dilsopropylamine and 5 mL of tetrahydrofuran was added dropwise to 30 ml (45 mmol) of n-butyllithium/hexane (1.5 mol/L) with stirring at 5° C. and the mixture was stirred for 1 hour to prepare a lithium diisopropylamide solution.

In 8.0 ml of tetrahydrofuran were suspended 1.57 g (10 mmol) of ethyl (3S)-4-cyano-3-hydroxybutyrate, 2.32 g (20 mmol) of tert-butyl acetate and 2.86 g (30 mmol) of magnesium chloride, and the suspension was stirred in an argon atmosphere at 0 to 5° C. To this solution, the lithium diisopropylamide solution prepared above was added dropwise over 30 minutes, and the mixture was further stirred at 5 to 20° C. for 16 hours.

In a separate vessel, 35 mL of 3 N-hydrochloric acid was mixed with 30 mL of ethyl acetate under stirring and the above reaction mixture was poured. After standing, the organic layer was separated, washed with saturated aqueous sodium chloride solution, and dried over anhydrous magnesium sulfate. The solvent was then distilled off under reduced pressure.

The residue was purified by silica gel column chromatography (Merck's Kieselgel 60, hexane:ethyl acetate=3:1) to give 1041 mg of tert-butyl (5S)-6-cyano-5-hydroxy-3-oxohexanoate (red oil) in 46% yield.

Example 8

Tert-butyl (5S)-6-cyano-5-hydroxy-3-oxohexanoate

Under argon gas, a solution composed of 3.90 g (38.5 mmol) of diisopropylamine and 3 mL of tetrahydrofuran was added dropwise to 22.9 mL (35 mmol) of n-butyllithium/hexane (1.5 mol/L) with stirring at 5° C. and the mixture was stirred for 1 hour to prepare a lithium diisopropylamide solution.

In 3.0 mL of tetrahydrofuran were dissolved 1.57 g (10 mmol) of ethyl (3S)-4-cyano-3-hydroxybutyrate and 2.32 g (20 mmol) of tert-butyl acetate, and the solution was stirred in an argon atmosphere at 0 to 5° C. To this solution was added 5.7 g (10 mmol) of a solution of tert-butylmagnesium chloride in toluene/tetrahydrofuran (1:2.5, by weight) (1.75 mol/kg) dropwise over 10 minutes, and the mixture was further stirred at 5° C. for 50 minutes. Then, the lithium diisopropylamide solution prepared above was added dropwise over 30 minutes and the mixture was further stirred at 5 to 20° C. for 16 hours.

In a separate vessel, 30 mL of 3 N-hydrochloric acid and 30 mL of ethyl acetate were mixed together under stirring and the above reaction mixture was poured. After standing, the organic layer was separated, washed with saturated aqueous sodium chloride solution, and dried over anhydrous magnesium sulfate. The solvent was then distilled off under reduced pressure.

The residue was purified by silica gel column chromatography (Merck's Kieselgel 60, hexane:ethyl acetate=3:1) to give 1302 mg of tert-butyl (5S)-6-cyano-5-hydroxy-3-oxohexanoate (red oil) in 57% yield.

Example 9

Tert-butyl (5S)-5,6-dihydroxy-3-oxohexanoate

Under argon gas, a solution composed of 5.01 g (49.5 mmol) of diisopropylamine and 5 mL of tetrahydrofuran was added dropwise to 30 mL (45 mmol) of n-butyllithium/hexane (1.5 mol/L) with stirring at 5° C. and the mixture was stirred for 1 hour to prepare a lithium diisopropylamide solution.

In 8.0 ml of tetrahydrofuran were suspended 1.02 g (10 mmol) of (3S)-3-hydroxybutyrolactone and 2.32 g (20 mmol) of tert-butyl acetate, and the suspension was stirred in an argon atmosphere at 0 to 5° C. To this solution, the above lithium diisopropylamide solution was added dropwise over 30 minuets, and the mixture was further stirred at 5 to 20° C. for 16 hours.

In a separate vessel, 35 mL of 3 N-hydrochloric acid and 30 mL of ethyl acetate were mixed together under stirring and the above reaction mixture was poured. After standing, the organic layer was separated, washed with saturated aqueous sodium chloride solution, and dried over anhydrous magnesium sulfate. The solvent was then distilled off under reduced pressure.

The residue was purified by silica gel column chromatography (Merck's Kieselgel 60, hexane:ethyl acetate=2:1) to give 124 mg of tert-butyl (5S)-5,6-dihydroxy-3-oxohexanoate (yellow oil) in 6% yield.

$^1$H-NMR (CDCl$_3$, 400 MHz/ppm): 1.48 (9H, s), 2.668–2.83 (2H, m), 3.0–3.8 (2H, bs), 3.42 (2H, s), 4.02–4.17 (2H, m), 4.40 (1H, m)

$^{13}$C-NMR (CDCl$_3$, 400 MHz/ppm): 27.8, 45.7, 51.0, 65.6, 68.0, 82.3, 166.4, 203.4

Example 10

Tert-butyl (5S)-5,6-dihydroxy-3-oxohexanoate

Under argon gas, a solution composed of 3.90 g (38.5 mmol) of diisopropylamine and 3 mL of tetrahydrofuran was added dropwise to 22.9 mL (35 mmol) of n-butyllithium/hexane (1.5 mol/L) with stirring at 5° C. and the mixture was stirred for 1 hour to prepare a lithium diisopropylamide solution.

In 3.0 mL of tetrahydrofuran were dissolved 1.02 g (10 mmol) of (3S)-3-hydroxybutyrolactone and 2.32 g (20 mmol) of tert-butyl acetate, and the solution was stirred in an argon atmosphere at 0 to 5° C. To this solution was added 5.7 g (10 mmol) of a solution of tert-butylmagnesium chloride in toluene/tetrahydrofuran (1:2.5, by weight) (1.75 mol/kg) dropwise over 10 minutes, and the mixture was further stirred at 5° C. for 50 minutes. Then, the lithium diisopropylamide solution prepared above was added dropwise over 30 minutes and the mixture was further stirred at 5 to 20° C. for 16 hours.

In a separate vessel, 30 mL of 3 N-hydrochloric acid and 30 mL of ethyl acetate were mixed together under stirring and the above reaction mixture was poured. After standing, the organic layer was separated, washed with saturated aqueous sodium chloride solution, and dried over anhydrous magnesium sulfate. The solvent was then distilled off under reduced pressure.

The residue was purified by silica gel column chromatography (Merck's Kieselgel 60, hexane:ethyl acetate=2:1) to give 980 mg of tert-butyl (5S)-5,6-dihydroxy-3-oxohexanoate (red oil) in 48% yield.

INDUSTRIAL APPLICABILITY

The present invention, constituted as described above, enables the production of 5-hydroxy-3-oxopentanoic acid derivatives, which are of use as pharmaceutical intermediates, particularly intermediates of HMG-CoA rductase inhibitors, from inexpensive, readily available starting compounds at a non-very-low temperature.

What is claimed is:

1. A process for producing a 5-hydroxy-3-oxopentanoic acid derivative of the following formula (IV):

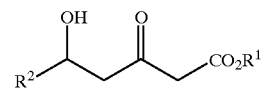

(IV)

wherein R$^1$ represents any of an alkyl group of 1 to 12 carbon atoms, an aryl group of 6 to 12 carbon atoms and an aralkyl group of 7 to 12 carbon atoms; and R$^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group, which comprises permitting a lithium amide of the following formula (III):

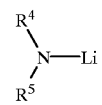

(III)

wherein R$^4$ and R$^5$ may be the same or different and each represents any of an alkyl group of 1 to 12 carbon atoms, an aryl group of 6 to 12 carbon atoms, an aralkyl group of 7 to 12 carbon atoms and a silyl group, to act upon a mixture of an acetic acid ester of the following formula (I) and a 3-hydroxypropionic acid derivative of the following formula (II) at a temperature not below −20° C.:

$$CH_3CO_2R^1 \qquad \qquad (I)$$

wherein R$^1$ represents any of an alkyl group of 1 to 12 carbon atoms, an aryl group of 6 to 12 carbon atoms and an aralkyl group of 7 to 12 carbon atoms:

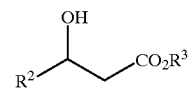

(II)

wherein R$^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group; R$^3$ represents any of an alkyl group of 1 to 12 carbon atoms, an aryl group of 6 to 12 carbon atoms and an aralkyl group of 7 to 12 carbon atoms; and R$^2$ and R$^3$ may be joined to each other to form a ring.

2. The process according to claim 1 wherein, referring to the lithium amide, R$^4$ and R$^5$ each represents an isopropyl group.

3. The process according to claim 1 wherein, referring to the acetic acid ester, R$^1$ represents a tert-butyl group.

4. The process according to claim 1, wherein a magnesium halide is added in permitting the lithium amide to act.

5. The process according to claim 4
wherein magnesium chloride is used as the magnesium halide.

6. A process for producing a 5-hydroxy-3-oxopentanoic acid derivative of the following formula (IV):

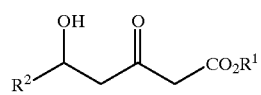

(IV)

wherein $R^1$ represents any of an alkyl group of 1 to 12 carbon atoms, an aryl group of 6 to 12 carbon atoms and an aralkyl group of 7 to 12 carbon atoms; and $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group, which comprises treating a mixture of an acetic acid ester of the following formula (I) and a 3-hydroxypropionic acid derivative of the following formula (II):

(I)

wherein $R^1$ represents any of an alkyl group of 1 to 12 carbon atoms, an aryl group of 6 to 12 carbon atoms and an aralkyl group of 7 to 12 carbon atoms:

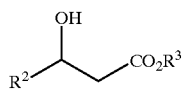

(II)

wherein $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group; $R^3$ represents any of an alkyl group of 1 to 12 carbon atoms, an aryl group of 6 to 12 carbon atoms and an aralkyl group of 7 to 12 carbon atoms; and $R^2$ and $R^3$ may be joined to each other to form a ring, with a Grignard reagent of the following formula (V):

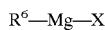

(V)

wherein $R^6$ represents any of an alkyl group of 1 to 12 carbon atoms, an aryl group of 6 to 12 carbon atoms and an aralkyl group of 7 to 12 carbon atoms; and X represents halogen, to prepare a mixture of a compound of the following formula (VI) and an acetic acid ester of the above formula (I):

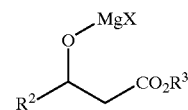

(VI)

wherein $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group; $R^3$ represents any of an alkyl group of 1 to 12 carbon atoms, an aryl group of 6 to 12 carbon atoms and an aralkyl group of 7 to 12 carbon atoms; $R^2$ and $R^3$ may be joined to each other to form a ring; and X represents a halogen atom, and permitting a lithium amide of the following formula (III):

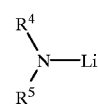

(III)

wherein $R^4$ and $R^5$ may be the same or different and each represents any of an alkyl group of 1 to 12 carbon atoms, an aryl group of 6 to 12 carbon atoms, an aralkyl group of 7 to 12 carbon atoms and a silyl group to act upon the mixture at a temperature not below −20° C.

7. The process according to claim 6
wherein, referring to the lithium amide, $R^4$ and $R^5$ each is an isopropyl group.

8. The process according to claim 6
wherein, referring to the acetic acid ester, $R^1$ represents a tert-butyl group.

9. The process according to claim 6,
wherein, referring to the Grignard reagent, $R^6$ represents a tert-butyl group and X represents a chlorine atom.

10. A process for producing a 5-hydroxy-3-oxopentanoic acid derivative of the following formula (IV):

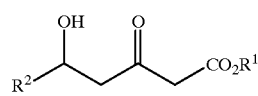

(IV)

wherein $R^1$ represents any of an alkyl group of 1 to 12 carbon atoms, an aryl group of 6 to 12 carbon atoms and an aralkyl group of 7 to 12 carbon atoms; and $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group, which comprises permitting a lithium amide of the following formula (III):

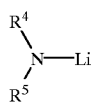

(III)

wherein $R^4$ and $R^5$ may be the same or different and each represents any of an alkyl group of 1 to 12 carbon atoms, an aryl group of 6 to 12 carbon atoms, an aralkyl group of 7 to 12 carbon atoms and a silyl group, to act upon a mixture of an acetic acid ester of the following formula (I) and a compound of the following formula (VI) at a temperature not below −20° C.:

(I)

wherein $R^1$ represents any of an alkyl group of 1 to 12 carbon atoms, an aryl group of 6 to 12 carbon atoms and an aralkyl group of 7 to 12 carbon atoms:

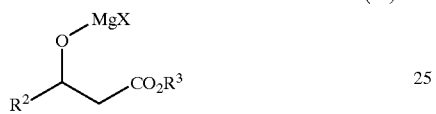

(VI)

wherein $R^2$ represents any of hydrogen, an alkyl group of 1 to 12 carbon atoms which may have a substituent, an alkenyl group of 2 to 12 carbon atoms which may have a substituent, an aryl group of 6 to 12 carbon atoms which may have a substituent, an aralkyl group of 7 to 12 carbon atoms which may have a substituent, a cyano group, a carboxyl group and an alkoxycarbonyl group; $R^3$ represents any of an alkyl group of 1 to 12 carbon atoms, an aryl group of 6 to 12 carbon atoms and an aralkyl group of 7 to 12 carbon atoms; $R^2$ and $R^3$ may be joined to each other to form a ring; and X represents a halogen atom.

11. The process according to claim 10
wherein, referring to the lithium amide, $R^4$ and $R^5$ each represents an isopropyl group.

12. The process according to claim 10
wherein, referring to the acetic acid ester, $R^1$ represents a tert-butyl group.

13. The process according to claim 10,
wherein, referring to the compound (VI), X represents a chlorine atom.

14. The process according to claim 1
wherein $R^3$ is a methyl group or an ethyl group.

15. The process according to claim 1
wherein $R^2$ is a chloromethyl group, a cyanomethyl group or a benzyloxymethyl group.

16. The process according to claim 1
wherein $R^2$ and $R^3$ are joined to each other to form a methylene group.

17. The process according to claim 1
wherein the compound (II) or (VI) is optically active.

18. The process according to claim 2
wherein, referring to the acetic acid ester, $R^1$ represents a tert-butyl group.

19. The process according to claim 2
wherein a magnesium halide is added in permitting the lithium amide to act.

20. The process according to claim 3
wherein a magnesium halide is added in permitting the lithium amide to act.

* * * * *